United States Patent
Schuetzle et al.

(10) Patent No.: US 12,241,026 B2
(45) Date of Patent: *Mar. 4, 2025

(54) PROCESS FOR THE SYNTHESIS OF HIGH-VALUE, LOW CARBON CHEMICAL PRODUCTS

(71) Applicant: Greyrock Technology, LLC, Sacramento, CA (US)

(72) Inventors: Robert Schuetzle, Sacramento, CA (US); Dennis Schuetzle, Grass Valley, CA (US); Orion Hanbury, Sacramento, CA (US)

(73) Assignee: Greyrock Technology, LLC, Sacramento, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/445,549

(22) Filed: Oct. 6, 2023

(65) Prior Publication Data

US 2024/0084201 A1 Mar. 14, 2024

Related U.S. Application Data

(63) Continuation of application No. 17/803,277, filed on Apr. 18, 2022.

(51) Int. Cl.
*C10G 2/00* (2006.01)
*C07C 1/04* (2006.01)
(Continued)

(52) U.S. Cl.
CPC .............. *C10G 2/32* (2013.01); *C07C 1/0475* (2013.01); *C07C 7/04* (2013.01); *C07C 7/12* (2013.01); *C07C 9/14* (2013.01); *C07C 9/22* (2013.01); *C07C 11/02* (2013.01); *C10G 50/02* (2013.01); *C10G 2300/302* (2013.01); *C10G 2300/4006* (2013.01); *C10G 2300/4012* (2013.01); *C10G 2300/4018* (2013.01); *C10G 2400/10* (2013.01)

(58) Field of Classification Search
CPC .. C10G 2/32; C10G 50/32; C10G 2300/4006; C10G 2300/4012; C10G 2300/4018; C10G 2400/10; C07C 11/02; C07C 9/22; C07C 9/14; C07C 7/12; C07C 7/04
See application file for complete search history.

(56) References Cited

U.S. PATENT DOCUMENTS

8,394,862 B1 3/2013 Schuetzle et al.
8,513,313 B2 8/2013 Huyser et al.
(Continued)

*Primary Examiner* — Jafar F Parsa
(74) *Attorney, Agent, or Firm* — McKinney Law Group APC; Jeffrey A. McKinney (57) ABSTRACT

The present invention describes improved processes for the synthesis of high value chemical products from low carbon syngas. In one aspect, a process for the production of chemicals is provided. The process comprises the following: feeding a feedstock comprising hydrogen and carbon monoxide to a liquid fuel production reactor, wherein the liquid fuel production reactor comprises a catalyst, thereby producing a product, wherein the product comprises a liquid phase and a solid phase, and wherein the liquid phase comprises C5-C23 hydrocarbons and oxygenated hydrocarbons, and wherein the solid-phase comprises C24-C45 aliphatic hydrocarbons, and wherein the liquid phase is between 51 percent by volume and 99 percent by volume of the product.

24 Claims, 2 Drawing Sheets

(51) Int. Cl.
*C07C 7/04* (2006.01)
*C07C 7/12* (2006.01)
*C07C 9/14* (2006.01)
*C07C 9/22* (2006.01)
*C07C 11/02* (2006.01)
*C10G 50/02* (2006.01)

(56) References Cited

U.S. PATENT DOCUMENTS

| | | |
|---|---|---|
| 9,090,831 B2 | 7/2015 | Schuetzle et al. |
| 2010/0077655 A1* | 4/2010 | Bauldreay ............... C10L 1/04 44/437 |
| 2018/0037824 A1* | 2/2018 | Schuetzle ............... C01B 3/02 |

* cited by examiner

PROCESS FOR THE SYNTHESIS OF HIGH-VALUE, LOW CARBON CHEMICAL PRODUCTS

This application is a continuation of U.S. patent application Ser. No. 17/803,277, filed on Apr. 18, 2022, which is incorporated by reference for all purposes.

FIELD OF THE INVENTION

The present invention describes improved processes for the synthesis of high value chemical products from low carbon syngas. The first step of the process involves the catalytic reaction of syngas in a liquid fuel production (LFP) catalytic reactor with an advanced catalyst that primarily produces $C_5$-$C_{23}$ liquid products with a minimal concentration of wax ($C_{24}$+ hydrocarbons), and a maximum concentration of normal 1-alkenes. The LFP $C_5$-$C_{23}$ liquid products ("liquid products") and the LFP $C_{24}$+ solid products are further processed to produce high value chemical products. When renewable or low carbon feedstocks are used, these chemical products have the additional benefit of being high value, green synthetic chemicals. Additional processing comprises at least one of a number of processing steps including: 1) separation of specific high-value normal paraffins, normal 1-olefins, and normal 1-hydroxy-alkanes from the $C_5$-$C_{23}$ liquid products using distillation, and/or solid adsorbents; 2) processing the $C_5$-$C_{23}$ liquid products in a catalytic oligomerization reactor to convert the normal 1-olefins into lubricants and separating the lubricants from the unconverted $C_5$-$C_{23}$ liquid products; 3) converting the normal 1-olefins into normal 1-hydroxy alkanes; and 4) converting the $C_5$-$C_{23}$ liquid products into jet fuel using catalytic hydro-processing and then distilling the hydro-processed product into jet fuel, diesel fuel and naphtha. In addition, post processing of both the liquid products and the solid products can provide a variety of high value products including solvents, n-paraffins, alpha olefins, lubricants, ethylene and propylene, polyethylene and polypropylene, high-performance waxes (e.g., ski wax), packaging, paints, coatings, cosmetics, flavors and fragrances, dyes, plastic resin production, consumer products and other high value chemicals.

BACKGROUND OF THE INVENTION

Mixtures of $H_2$ and CO are called synthesis gas or syngas. Syngas can be made from many different sources. Coal can be gasified to produce syngas; natural gas can be reformed with steam or with oxygen in an autothermal reformer or partial oxidation system to produce syngas; and biomass such as woody biomass, agricultural residues or other organic matter as well as municipal wastes can be gasified to produce syngas. Pyrolysis systems can be used to produce syngas and other products, such as pyrolysis oils, from biomass. Hydrogen can be produced from the electrolysis of water and carbon monoxide can be produced from carbon dioxide and hydrogen by the reverse water gas shift (RWGS) reaction. The RWGS reaction is also referred to as $CO_2$ hydrogenation.

Syngas may be used as a feedstock for producing a wide range of chemical products, including liquid fuels, hydroxy alkanes (alcohols), acetic acid, dimethyl ether, olefins and many other chemical products. Syngas needs to be directly produced and converted at the production site to fuels and/or chemical products since it is not practical to transport the syngas to distant refineries and chemical processing plants.

The catalytic hydrogenation of carbon monoxide to produce light gases, liquids and waxes, ranging from methane to heavy hydrocarbons (C100 and higher) in addition to oxygenated hydrocarbons, is typically referred to Fischer-Tropsch (or F-T) synthesis. Traditional low temperature (<250° C.) F-T processes primarily produce a high molecular weight F-T wax ($C_{24}$-$C_{100}$) from the catalytic conversion process. These F-T waxes typically comprise about 65 volume % of the total carbon containing products. The other 35 volume % is comprised of $C_5$-$C_{23}$ liquid hydrocarbons. These F-T liquid hydrocarbons include normal alkanes and a small fraction of normal alkenes, normal hydroxy-alkanes (alcohols) and branched alkanes. Hydrocarbons in the $C_5$-$C_{12}$ range are typically referred to as naphthas.

The F-T waxes are hydrocracked and/or further processed to produce diesel, naphtha, and other products. During this hydrocracking process, light hydrocarbons are also produced, which may require additional upgrading to produce viable products (All et al, 2016).

There have been attempts to upgrade the value of the F-T liquid fraction to higher valued products. For example, UOP's Cat Poly process has been used to oligomerize the light olefins (alkenes) to diesel at Sasol's F-T plant in South Africa. The Cat Poly process uses a solid phosphoric acid (SPA) catalyst to convert the light olefins to diesel fuel. However, the oligomer product is highly branched and therefore has a low cetane index that must be blended with higher cetane index diesel to meet an overall diesel fuel specification (de Klerk, 2008). In addition, since the concentration of olefins in the F-T liquid fraction is small, it does not make economic sense to employ this approach.

Greyrock has developed an innovative catalyst that primarily produces a hydrocarbon product that is comprised of about 95 volume % of $C_1$-$C_{23}$ liquid hydrocarbons and up to 5 volume % of $C_{24}$-$C_{45}$ hydrocarbons (wax), depending on operating conditions of the catalyst (Schuetzle et al; U.S. Patents 2013, 2015, 2017, 2018, 2019; Canadian Patents 2017, 2018). This liquid hydrocarbon fraction consists primarily of normal aliphatic hydrocarbons, normal 1-alkenes, and normal 1-hydroxy alkanes.

Table 1 summarizes the relationship between $H_2$/CO syngas ratios and the concentrations of the naphtha, diesel, and wax fractions. The naphtha fraction is defined as the sum (in volume %) of $C_5$-$C_8$ hydrocarbons and 50% of the $C_9$ hydrocarbons. The diesel fraction is defined as the sum (in volume %) of 50% of the $C_9$ hydrocarbons and the $C_{10}$-$C_{23}$ hydrocarbons. The LFP solid products consist of normal aliphatic hydrocarbons (alkanes) ranging from $C_{24}$-$C_{45}$. As shown in Table 1, the abundance of the naphtha fraction does not change as the syngas $H_2$/CO ratio is reduced from 2.00/1.00 to 0.55/1.00. However, there is a slight decrease in the diesel fraction and an increase in the wax fraction as the $H_2$/CO ratio is reduced.

TABLE 1

The Distribution of Fuel Constituents as a Function of $H_2$/CO Ratios

| Syngas $H_2$/CO Ratio | 2.00 | 1.90 | 1.56 | 1.08 | 0.55 |
|---|---|---|---|---|---|
| Liquid Fuel Constituents (Volume %) | | | | | |
| Naphtha ($C_5$-$C_9$) | 28.8 | 29.3 | 29.3 | 28.4 | 28.6 |
| Diesel ($C_9$-$C_{23}$) | 66.9 | 66.5 | 65.3 | 64.5 | 63.5 |
| $C_{24}$ + Hydrocarbons | 4.3 | 4.2 | 5.4 | 7.1 | 7.9 |
| Total | 100.0 | 100.0 | 100.0 | 100.0 | 100.0 |

Table 2 summarizes the relationship between $H_2/CO$ ratios and the distribution of the normal alkanes, branched alkanes (iso-alkanes), normal 1-alkenes, and normal 1-hydroxy alkanes in the directly produced LFP liquid product (catalyst operating conditions: T: 415° F.; P: 315 psi; SV: 1,750). At a low $H_2/CO$ ratio of 0.55 the $C_5$-$C_{16}$ normal 1-alkenes are increased from 4.5 volume % to 34.8 volume %. However, there is not as much of a change in the abundance of the $C_3$-$C_{12}$ normal hydroxy alkanes (2.8-4.3 volume %), or iso-alkanes (5.8-8.2 volume %).

TABLE 2

The Distribution of Fuel Constituents in the LFP liquid fraction as a Function of $H_2/CO$ Ratios

| Syngas $H_2/CO$ Ratio | 2.00 | 1.90 | 1.56 | 1.08 | 0.55 |
|---|---|---|---|---|---|
| Liquid Fuel Constituents (Volume %) | | | | | |
| Total Normal Alkanes ($C_5$-$C_{23}$) | 86.9 | 84.8 | 75.9 | 68.4 | 52.7 |
| Total Iso-Alkanes ($C_5$-$C_{23}$) | 5.8 | 5.5 | 7.6 | 8.0 | 8.2 |
| Total Normal 1-Alkenes ($C_5$-$C_{16}$) | 4.5 | 6.8 | 12.3 | 17.4 | 34.8 |
| Total Normal 1-Hydroxy-Alkanes ($C_3$-$C_{16}$) | 2.8 | 2.9 | 4.2 | 4.8 | 4.3 |
| Total | 100.0 | 100.0 | 100.0 | 100.0 | 100.0 |

Since typical F-T processes primarily produce a solids fraction ($C_{24}$-$C_{100}$) and liquids fraction ($C_5$-$C_{23}$) that comprises about 65 volume % and 35 volume % of the total $C_5$+ products, respectively (Gruber et al, 2019; Fedou et al, 2020), there has been no economic incentive to convert this minor liquid fraction into higher value products. As a result, there is very little prior art related to the conversion of these liquids to higher value products.

Table 3 compares the abundance of chemical constituents produced from the catalytic conversion syngas by this Improved LFP Process compared to typical F-T processes. F-T processes produce normal 1-alkenes and normal 1-hydroxy-alkanes in low concentrations that average about 3.0 and 1.0 volume %, respectively. Therefore, it is not economical to separate specific normal 1-alkenes and normal 1-hydroxy-alkanes from the liquids fraction.

Table 3 compares the chemical constituents produced from the conversion of syngas using this Improved LFP Process. This process was operated using a low syngas $H_2/CO$ ratio of about 0.55 which significantly increased the production of normal 1-alkenes to about 35 volume % of the total liquids and solids fractions. Although the solids fraction for the improved LFP process only produces about 8.0 volume % of normal alkanes (waxes), this wax has a higher economical value than typical F-T waxes.

Since F-T produces normal alkanes at about 30 volume %, little or no art has been reported on the development of processes for the upgrading of this minor fraction into higher value products. Instead, several processes have been described for upgrading the combined liquid and solid products.

Farshid et al (2009) separated products, from the F-T catalytic conversion of syngas, into a condensate (liquids) fraction and a heavy (solids) fraction. They subjected the solids fraction to hydrocracking using multiple catalyst beds to reduce the carbon chain length. The products from this hydrocracking were then combined with the liquids fraction. This combined fraction was then processed using traditional oil refinery processes to produce fuels and middle distillates.

Tanaka et al (2015) describes the distillation of the combined liquid and solids fractions into a middle distillate and a wax fraction. The middle distillate fraction was then distilled into a second middle distillate and a light distillate fraction. Since F-T middle distillates are comprised of low concentrations of normal 1-alkenes and normal 1-hydroxy alkanes (Table 3), they did not attempt to separate these species from the normal alkanes.

In contrast, this Improved LFP Process primarily produces a high proportion (>90 volume %) of liquid hydrocarbons (compared to about 35 volume % for F-T processes) so that processing of the heavy fraction (e.g., waxes) are not necessary. In addition, the operating conditions of the Improved LFP Process can be easily adjusted to produce a high abundance (about 32 volume % or greater) of normal 1-alkenes (compared to about 3 volume % for F-T processes) (Table 3).

TABLE 3

A Comparison of Chemical Constituents Produced from the Conversion of Syngas by this Improved LFP Process compared to Typical F-T Processes

| Syngas Conversion Technology | Normal Alkanes | Iso-Alkanes | Normal 1-Alkenes | Normal 1-Hydroxy Alkanes | Total |
|---|---|---|---|---|---|
| | | | Volume % | | |
| Improved LFP Process | | | | | |
| Liquids Fraction (C5-C23) | 49 | 7 | 32 | 4 | 92 |
| Solids Fraction (C24-C45) | 8 | 0 | 0 | 0 | 8 |
| Total | 57 | 7 | 32 | 4 | 100 |
| Typical F-T Process (1) | | | | | |
| Liquids Fraction (C5-C23) | 28 | 3 | 3 | 1 | 35 |
| Solids Fraction (C24-C100) | 54 | 11 | 0 | 0 | 65 |
| Total | 82 | 14 | 3 | 1 | 100 |

(1) Schultz-Flory F-T chain growth probability (alpha) of 0.95

SUMMARY OF INVENTION

The invention relates to a process to directly convert syngas to liquid fuels in a catalytic Liquid Fuels Production (LFP) reactor with a novel catalyst that primarily produces a mixture of $C_5$-$C_{23}$ hydrocarbons of 75 volume % or more, 80% volume % or more, 90% volume, or more preferably 95% or more with a limited proportion of hydrocarbons that are heavier than $C_{24}$, 25 volume % or less, 20% volume or less, 10% volume or less, or more preferably 5% volume or less, when the catalyst is run under conditions of Hz/CO: 2.1, temperature: 415° F.; pressure: 315 psi; and hourly space velocity: 1,750.

The LFP product is processed to produce chemical products that have a much higher economic value than diesel fuel and naphtha. This processing comprises at least one of a number of additional steps comprising: 1) separation by distillation of specific normal paraffins (or n-alkanes) from the LFP product; 2) separation by distillation of specific normal 1-alkenes (or 1-alkenes) from the LFP product; 3) separation by distillation of normal 1-hydroxyalkanes from the LFP product; 4) catalytic hydration of the olefins in the LFP product to normal hydroxy-alkanes; and (5) catalytic oligomerization of the olefins in the LFP product into lubricants. Some embodiments of the invention involve combinations of these five processing steps. The LFP product can be simply distilled into LFP naphtha and LFP diesel products.

Table 4 summarizes the commercial value of the LFP naphtha and LFP diesel compared to some of the specific chemical products that can be produced as described in this document. These commercial values are subject to change and do not include any regulatory incentives like low carbon credits including RINs, LCFS, or other possible environmental credits.

The LFP naphtha and LFP diesel have commercial values that are similar to crude oil as exemplified in the price of West Texas Intermediate (WTI) crude oil pricing. Table 4 also provides the commercial values of other possible products that can be produced from the LFP product as described in this document. The second column in Table 4 shows the ratio of the price of various products to the value of WTI crude oil. As can be seen, all the other products listed in the table have current commercial values that are up to about 280 times higher than the LFP product, LFP naphtha and LFP diesel.

TABLE 4

Commercial Value (Fourth Quarter 2020) for Potential LFP Chemical Products

| Chemical | $USD/MT (1) | Value Ratio (to Crude Oil) | Uses |
| --- | --- | --- | --- |
| WTI Crude Oil | 289 | 1.00 | chemical and fuel feedstock |
| LFP Naphtha | 323 | 1.12 | chemical and fuel feedstock |
| LFP Diesel | 385 | 1.33 | diesel engine fuel |
| 1-butanol | 800-2,400 (2) | 2.77-8.30 | flavors and fragrances |
| 1-pentanol | 30,000-60,000 (2) | 103.8-207.6 | flavors and fragrances |
| 1-hexanol | 5,600-14,800 (2) | 19.4-51.2 | flavors and fragrances |
| 1-heptanol | 10,000-50,000 (2) | 34.6-173.0 | flavors and fragrances |
| 1-octanol | 20,000-80,000 (2) | 69.2-276.8 | flavors and fragrances |
| 1-hexene | 10,000-30,000 (2) | 34.6-103.8 | dye intermediate; plastic resin production; fragrances |
| Mineral Spirits | 2,850 (3) | 9.86 | paint thinners; paint removers; adhesives and coatings; degreasers; charcoal lighter fluid |
| Group 24cSt lubricants | 22,400 (4) | 77.5 | compressor, engine and hydraulic oils |

(1) USD is United States Dollar; MT is metric ton = 1000 kg;
(2) These current (November 2021) commercial values are from www.alibaba.com for industrial grade (>98% purity) in metric ton quantities without any incentives, RINS, LCFS or other credits.
(3) This commercial value is for 55-gallon quantities of mineral spirits with less than 1% aromatic content (www.chemcentral.com)
(4) This commercial value is for 55-gallon quantities of group 23cSt lubricants (www.grainger.com)

In the normal paraffin separation embodiment, the unfractionated LFP product comprises a mixture of $C_5$-$C_{23}$ n-paraffins (Table 1). N-paraffins have economic value as industrial solvents. For example, n-heptane is an environmentally safer solvent than hexane or benzene or toluene. The LFP reactor may be operated in a manner to increase the n-paraffin production at the expense of the 1-alkenes and alcohols in the LFP Naphtha. This can be done by increasing the hydrogen to carbon monoxide in the LFP reactor feed as described in Table 2. The LFP product can be further processed in a distillation column or a series of distillations columns that uses boiling point differences to separate the various n-paraffins since the boiling point of hexane is 65° C., while the boiling point of heptane is 98° C. The boiling points of other components are also different than heptane. The boiling point of heptane is 94° C. and the boiling point of octane is 126° C. In this manner, industrial grade n-heptane can be produced as a product from the LFP liquid product. The n-heptane will have a purity of at least 95 vol. %, more preferably greater than 98 vol. %, or even more preferably better than 99 vol. It should be noted that all the n-paraffin products have wholesale prices that in are in excess of the unfractionated LFP liquid product.

In the normal 1-alkene separation embodiment, the LFP liquid product is comprised of a mixture of 1-alkenes as summarized in Table 2. The LFP reactor may be operated in a manner to increase the 1-alkene production at the expense of n-paraffins up to about 34 volume % or greater. This is done by decreasing the hydrogen to carbon monoxide ratio in the LFP reactor syngas feed and also can be influenced by temperature, pressure and flow/gas hourly space velocity.

In the normal 1-hydroxy alkane separation embodiment, the LFP liquid product is comprised of a mixture of $C_3$-$C_{16}$ normal 1-hydroxy alkanes. Although reducing the syngas $H_2$/CO ratio increases their concentration from 2.8 to 4.3 vol. %, their abundance is still quite low (Table 2). However, as shown in Table 3, the commercial values of the normal 1-hydroxy alkanes are quite attractive.

Since some of the normal 1-hydroxy alkanes typically have a higher commercial value than the normal 1-alkenes, the normal 1-alkenes can be converted to normal 1-hydroxy alkanes by catalytic hydration. Molybdenum and tungsten hetero-polyacids impregnated on zeolite substrates are used as the catalysts for this conversion. The reaction proceeds with high selectivity at about 300 psi and about 550° F.

In another embodiment, the normal 1-alkenes are converted to synthetic lubricating oil. This is carried out by converting the normal 1-alkenes in the unfractionated LFP product to various kinds of synthetic lubricating oils by using catalytic oligomerization. Various viscosities of lubricating oils are produced by modifying the operating conditions of the oligomerization process. The lubricating oil is easily separated from the unconverted fuel by distillation.

DETAILED DESCRIPTION OF INVENTION

The invention relates to a process to convert syngas directly to liquid fuels in a catalytic Liquid Fuels Production (LFP) reactor with a novel catalyst that primarily produces a mixture of $C_5$-$C_{23}$ hydrocarbons (referred to as LFP products in this document) but with less than about 10 vol % of hydrocarbons that a molecular weight greater than $C_{24}$ and preferably less than about 5 vol % of hydrocarbons. Product selectivity can be tailored based on plant operating conditions and market off-take opportunities.

In one embodiment, the syngas is a low carbon syngas derived from the conversion of biomass or other renewable sources by gasification or low carbon syngas derived from a process that converts captured carbon dioxide or a process that converts biogas into syngas or a process that converts any other low carbon material into syngas. In this embodiment, the syngas is produced using a catalytic RWGS reaction to convert carbon dioxide and hydrogen into carbon monoxide and water. The hydrogen can be produced from numerous sources including from the electrolysis of water. After cooling to remove water, the desired dry synthesis gas (i.e., syngas) is comprised of CO and unconverted $H_2$ and $CO_2$.

One embodiment of the invention involves a Liquid Fuels Production (LFP) reactor system. This is also known as the hydrocarbon synthesis step. The LFP reactor primarily converts CO and $H_2$ into $C_5$-$C_{23}$ hydrocarbons that can be used as liquid fuels and/or chemicals.

The LFP reactor is a multi-tubular fixed bed reactor system. Each LFP reactor tube can be between 13 mm and 26 mm in diameter. The length of the reactor tube is generally greater than 6 meters in length and more preferably greater than 10 meters in length. The LFP reactors are generally vertically oriented with LFP reactor feed entering at the top of the LFP reactor. However, horizontal reactor orientation is possible in some circumstances and setting the reactor at an angle may also be advantageous in some circumstances where there are height limitations. Most of the length of the LFP reactor tube is filled with LFP catalyst. The LFP catalyst may also be blended with diluent such as silica or alumina to aid in the distribution of the LFP reactor feed into and through the LFP reactor tube and to control heat profiles. The chemical reaction that takes place in the LFP reactor produces an LFP product gas that comprises liquid hydrocarbon products from five to twenty-three carbons in length ($C_5$-$C_{23}$ hydrocarbons) as well as water. Less than 2% of the carbon monoxide in the LFP reactor feed is converted to carbon dioxide in the LFP reactor. It is also important that only a limited amount of the carbon monoxide in the LFP reactor feed be converted to hydrocarbons with a carbon number greater than $C_{24}$.

The LFP catalyst used in an embodiment of this invention, however, primarily produces $C_5$-$C_{23}$ hydrocarbons with a minimal concentration of $C_{24}$+ hydrocarbons (less than 25 volume %, less than 10 volume % and preferably less than about 5 volume %) compared to typical Fischer Tropsch (F-T) processes that produce about 65 vol % of $C_{24}$-$C_{100}$ hydrocarbons. Often times in typical F-T processes, waxes can exceed $C_{100}$. The LFP catalyst is supported on a metal oxide support that is chosen from a group of alumina, silica, titania, activated carbon, carbon nanotubes, zeolites or other support materials with sufficient size, shape, pore diameter, surface area, crush strength, effective pellet radius, or mixtures thereof. The catalyst can have various shapes of various lobed supports with three, four, or five lobes with two or more of the lobes being longer than the other two shorter lobes, with both the longer lobes being symmetric. The distance from the mid-point of the support or the mid-point of each lobe is called the effective pellet radius which is an important parameter to achieve the desired selectivity to the $C_5$ to $C_{23}$ hydrocarbons. The LFP catalyst promoters may include one of the following: cerium, ruthenium, lanthanum, platinum, rhenium, gold, silver, nickel, or rhodium. These promoters may be used individually or in combination with each other. The LFP catalyst promoters are less than 1 wt. % of the total catalyst and preferably less than 0.5 wt. % and even more preferably less than 0.1 wt. %.

The LFP catalyst support has a pore diameter greater than 8 nanometers (nm), a mean effective pellet radius of less than 60 micrometers (um), a crush strength greater than 3 lbs./mm and a BET surface area of greater than 150 $m^2/g$. The catalyst after metal impregnation has a metal dispersion of about 4%.

The LFP fixed bed reactor is operated in a manner to maximize the $C_5$-$C_{23}$ hydrocarbon and oxygenated hydrocarbon yield. The LFP reactor in one embodiment is operated at pressures in the range of 11.4 to 32.0 bar (150 to 450 psig) and more typically 300-350 psi. The reactor is operated over a temperature range from 177° C. (350° F.) to 238° C. (460° F.) and more typically at about 210° C. (410° F.). Since the catalytic reaction is exothermic, the temperature of the reactor is maintained inside the LFP reactor tubes by the reactor tube bundle being placed into a heat exchanger where water is present on the outside of the LFP reactor tubes. The steam pressure is controlled in the shell side of the reactor and the temperature is at a lower temperature than the LFP reaction temperature so that heat flows from the LFP reactor tube to the lower temperature steam. The steam temperature is maintained by maintaining the pressure of the steam which is generally saturated steam.

Figure 1:
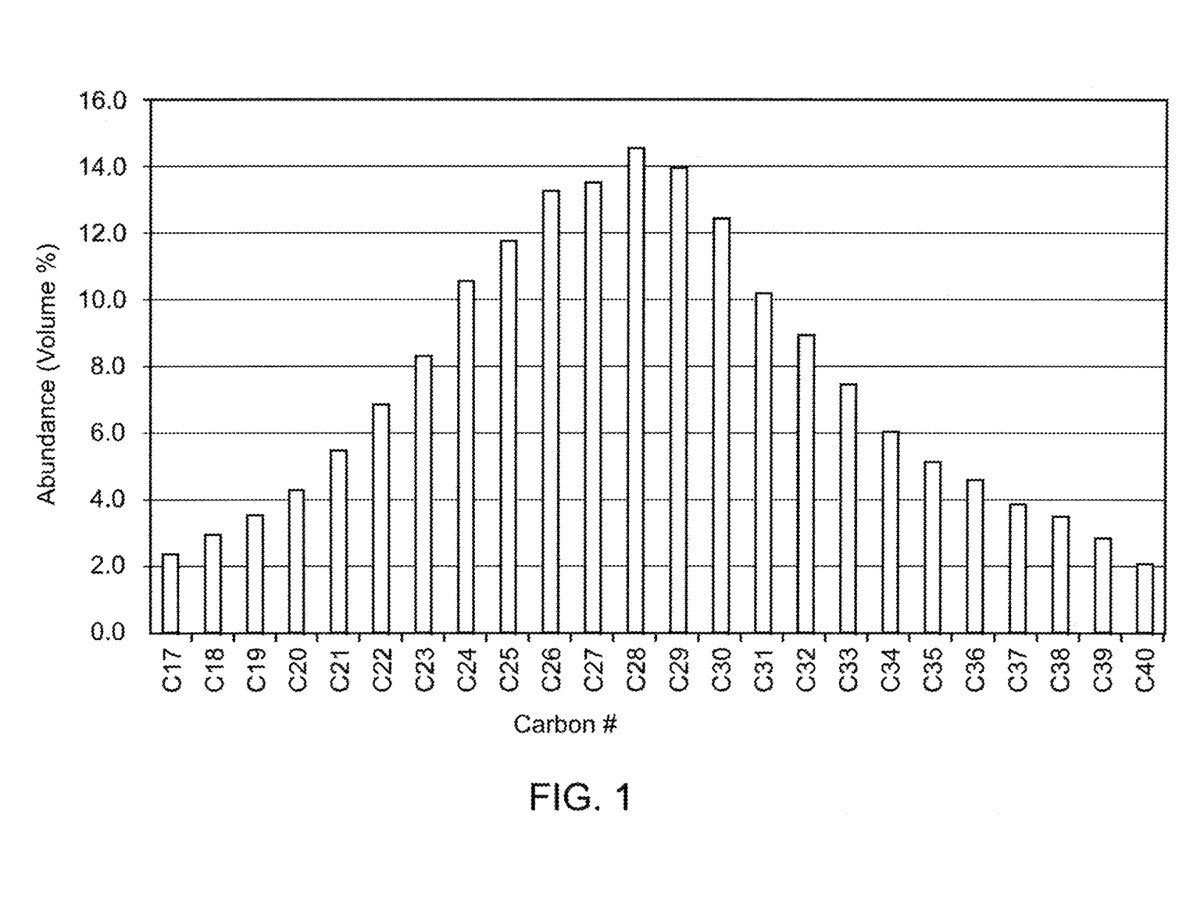
FIG. 1 shows the normal hydrocarbon distribution of the LFP Process Wax.

In another embodiment, the LFP reactor is operated in a mode to maximize normal 1-alkene production for use in a downstream oligomerization reactor. Although the LFP reactor is typically operated between a $H_2$/CO ratio (vol/vol) of 1.7 and 2.2 and a temperature near 210° C. (410° F.), the normal 1-olefin fraction of the LFP product can be increased by reducing the $H_2$/CO ratio as summarized previously in Table 2. Although operating at lower $H_2$/CO ratios significantly increases the concentration of normal 1-alkenes, there is also an increase of $C_{24}$+ hydrocarbons (wax) from about 4 to 8 vol. % (Table 2). As detailed in a later section, this is a light crystalline wax that consists primarily of $C_{24}$-$C_{40}$ normal aliphatic hydrocarbons as illustrated by FIG. 1.

This light crystalline wax is very different than the heavy non-crystalline waxes that are produced by traditional F-T processes. Such light crystalline waxes command a premium value since they are typically used as ski, car, furniture waxes and other products.

Operation of the LFP reactor is a balance of making small increases in temperature, potentially between 210° C. (410° F.) and 221° C. (430° F.) and reducing the $H_2$/CO ratio as low as 0.50/1.00 (Table 2) to create a maximized normal 1-olefin feedstock that can be used in the downstream oligomerization reactor.

The CO conversion in the LFP reactor is maintained at between 40 to 60 volume % CO per pass. CO can be recycled for extra conversion or sent to a downstream additional LFP reactor. The carbon selectivity to $CO_2$ is minimized to less than 4% of the converted CO and more preferably less than 1%. The carbon selectivity to $C_5$-$C_{24}$ hydrocarbons is between 60 and 85%. The LFP product contains the desired $C_5$-$C_{24}$ liquid aliphatic hydrocarbons and oxygenated hydrocarbons as well as unreacted carbon monoxide, hydrogen, a small amount of $C_1$-$C_4$ gas-phase hydrocarbons and a small amount of $C_{24+}$ hydrocarbons.

The LFP reactor product that contains the desired $C_5$-$C_{23}$ liquid hydrocarbons can be further processed in a separation system. The separation system can include distillation. The desired $C_5$-$C_{23}$ products can be used for gasoline blendstock, diesel fuel, jet fuel, or used as low-carbon chemicals that can displace chemicals derived from petroleum or natural gas. In one embodiment, the LFP product is sent to a series of fractionators are used to create a high cetane diesel fuel with an adjustable flash point between 38-54° C. (100-130° F.) and a stabilized naphtha (potentially a gasoline blend stock or chemical feedstock). A basic arrangement for these columns, which include:

A) Wax Stripper—This unit uses steam to recover fuel-range components from the waxy $C_{24}$+ material. The overhead fuel-range components and steam are sent to the main fractionator while the stripped wax is sent to heated storage The wax stripper is a column without a condenser or reboiler, operating at approximately 170° C. (340° F.) and with enough pressure, 40 psig, for the overhead vapors to enter the main fractionator column.

B) Main Fractionator—This column splits the raw fuel into naphtha and diesel range components to control the diesel flash point. This column includes a high pressure (HP) steam heated reboiler, and an external condenser with 3-phase separation for removing absorbed water and steam from the wax stripper feed.

C) Optional Naphtha Stabilizer—This process controls the Reid vapor pressure (RVP) to a specification of 8 psia. The stabilizer includes a low pressure (LP) steam reboiler, and an integrated knock-back, water-cooled condenser.

D) Optional Diesel Cold-Flow/Kerosene Vacuum Column—This process is used to adjust the diesel pour point for cold weather sales and/or produce a kerosene cut. The feed is heated to 300° C. (570° F.). The column is 20 stages with an overhead condenser pressure of 6 psia. The kerosene cut may be used as a jet fuel component. Under certain conditions the kerosene cut may meet the ASTM specification (ASTM D7566) for use as a jet fuel In one embodiment of the invention, the kerosene cut of the LFP liquid product does not meet all of the ASTM D7566 specifications for use as jet fuel, it may be necessary to perform light hydro-isomerization the LFP liquid product or a fraction of the LFP liquid product such as LFP kerosene or LFP light diesel to meet the specification for use as jet fuel. The LFP liquid product or a fraction of the product is pressurized and mixed with a stream comprising hydrogen. The hydrogen can be produced from the electrolysis of water or from the reforming of natural gas or from the gasification of waste or biomass or other methods to produce low carbon hydrogen.

The combined stream comprising hydrogen and at least a portion of the LFP liquid product is then heated and fed to the hydro-isomerization reactor. The hydro-isomerization reactor operates at an elevated pressure of greater than 100 psig but generally less than 2,000 psig. The hydro-isomerization reactor operates at a temperature of between 250° C. and 400° C. Products from the hydro-isomerization reactor are cooled before entering the hot separator where gas and liquid are separated in hot and cold separators.

The hydrocarbon products from the hot and cold separators are sent to the fractionation section where the light-ends and hydrocarbon products are separated. This fraction system may include a wax stripper and main fractionator as well as a naphtha stabilizer and a Kerosene vacuum column. The fractionators are operated in a manner such that the kerosene stream will meet the specifications of ASTM D7566.

In one embodiment of the invention, the economic value of the LFP liquid product is increased by at least one means including 1) through separating a stream from the LFP liquid product where that separated stream comprises at least 70 vol %, at least 80 vol %, or more preferably at least 95 vol. % of a an individual n-paraffin (e.g. n-heptane); 2) through separating a stream from the LFP liquid product where the separated stream comprises at least 70 vol %, at least 80 vol %, or more preferably at least 95 vol. % of a specific normal alpha-alkene; 3) through separating a stream from the LFP liquid product where the separated stream comprises at least 70 vol %, at least 80 vol %, or more preferably at least 95 vol. % of a specific normal hydroxy-alkane; 4) through further processing the LFP liquid product in an oligomerization reactor where at least a portion of the olefins in the liquid product are converted to lubricants or other hydrocarbon products with a viscosity Index of at least 80 and more preferably at least 95.

In one embodiment of the invention, the LFP reactor may be operated in a manner to increase the n-paraffin production at the expense of the normal 1-alkenes and normal 1-hydroxy-alkanes in the LFP liquid product. This can be done by increasing the hydrogen to carbon monoxide in the LFP reactor feed. The LFP liquid product can be further processed in a distillation column or two distillation columns that use the boiling point differences to separate the various n-paraffins. As an example, the boiling point of hexane is 65° C., while the boiling point of heptane is 98° C. The boiling point of other possible materials in the LFP liquid product is also different than heptane or the other desired products. The boiling point of heptane is 94° C. and the boiling point of octane is 126° C. In this way, industrial grade n-heptane can be produced as a product from the LFP liquid product. The n-heptane will have a purity of preferably greater than 95 vol. %, more preferably 98 vol. %, and even more preferably greater than 99 vol. %. Other n-paraffin products (e.g., n-hexane, n-octane, n-nonane, n-pentane, n-decane) may also be produced in a likewise manner with the same preferable purities.

In one embodiment of the invention, the LFP liquid product contains a mixture of normal 1-alkenes. The LFP reactor may be operated in a manner to increase the 1-alkene production at the expense of n-paraffins. This is done by decreasing the hydrogen to carbon monoxide ratio in the LFP reactor syngas feed (Table 2). The economic value of the LFP liquid products is increased through separating a stream from the LFP liquid product where the separated stream comprises at least 95 vol. % of a specific normal 1-alkene, preferably 98 vol % of a specific 1-alkene and even more preferably 99 vol. % of a specific normal 1-alkene. This separation is accomplished by distillation based on the difference of the normal boiling points of the various LFP liquid product components. Various $C_5$-$C_{16}$ normal 1-alkenes can be separated in this manner.

In one embodiment of the invention, the LFP liquid product is catalytically converted in an oligomerization reactor. The oligomerization reactor is a fixed bed tubular catalytic reactor system that operates as a trickle bed. Generally, the reactor is in a vertical orientation. Inert materials such as alumina balls or static mixers may be used at the inlet of the reactor to aid in even distribution of the liquid feedstock across the catalyst bed. Normal 1-alkenes in the LFP liquid product are oligomerized to longer chain hydrocarbons in the oligomerization reactor. At least some of the normal hydroxy alkanes in the LFP liquid product are also converted in the oligomerization reactor. The oligomerization reactor produces a mixture of higher molecular weight hydrocarbons. The oligomerization product is subsequently separated in a separation device into several products. In the present invention, the olefins in the LFP liquid product are oligomerized to lubricants with boiling points from 343-510° C. (650-950° F.).

There are a number of possible oligomerization catalysts that can be used in the present invention. In one embodiment of the invention, the catalyst is chromium impregnated on a silica substrate. The catalyst has between 0.5 and 5.0 weight % chromium with a preferred loading of approximately 1.0 weight % chromium as a fraction of the total catalyst weight. The silica support consists of a large pore silica gel. The catalyst is calcined in air at 800° C. for 16 hours. The catalyst can be reduced prior to use in the oligomerization reactor in a number of ways, the catalyst can be reduced with CO at 300° C. for 1.5 hours. The catalyst may also be reduced using syngas. Other possible catalysts include Ziegler-Natta or Metallocene catalysts as well as ZSM-5 and other silica-alumina materials.

The oligomerization reaction is exothermic. The operating temperature of the reactor is 120 to 160° C. Higher reaction temperatures reduce the viscosity of the lubricating base oil and can be used as a tool to control the viscosity of the lubricants. Pressures as low as atmospheric pressure can be used but an operating pressure of 18.2 to 24.5 bar (250-350 psig) is preferred.

Approximately greater than 70%, greater than 80%, or more preferably greater than 90% of the olefins in the LFP liquid product are converted to lubricants on a single pass. Some of the hydroxy-alkanes in the LFP liquid product are also converted to lubricants.

The oligomerized LFP liquid product will have limited amounts of olefins or oxygenates and in some embodiments, it will consist primarily of paraffins. As such the separation of the oligomerized product into specific normal paraffins is significantly easier than the separation of the normal paraffins in the unprocessed LFP liquid product since it will be less likely that the normal 1-alkenes and normal hydroxy alkanes will co-elute with the normal paraffins.

In one embodiment, the oligomerized LFP product is further processed in a reforming unit. The reforming unit converts the oligomerized LFP liquid product to syngas. The reforming unit uses steam to convert the oligomerized LFP liquid product to syngas. This syngas can be used as a portion of the LFP reactor feed.

The LFP liquid product is primarily comprised of straight chain paraffins when the LFP catalyst is used to convert syngas with an $H_2/CO$ of about 2.0, a temperature of about 410° F. and a pressure of about 325 psi (Table 2). In some embodiments, the oligomerization reaction will result in an oligomerized product with some branching. This will improve the cold flow properties of the diesel fraction.

Another fraction of the oligomerization product consists of lubricants. The lubricants consist of a mixture of hydrocarbons that generally have boiling points above 343° C. (650° F.). These lubricants are similar in nature to poly-alpha-olefins (PAO) with high viscosity index (VI). The viscosity Index is a measure of the temperature dependence of the kinematic viscosity of lubricants and is commonly measured by the methods defined in ASTM D2270. The higher the VI, the lower the temperature dependence of the viscosity and the better the lubricant works. The VI of the lubricants should have a VI of at least 95. The kinematic viscosity can be measured by a viscometer using the methods of ASTM D445. The kinematic viscosity at 100° C. of these lubricants should be at least 3.0 mm$^2$ per second.

Additional separation via distillation of the lubricants may be desired to obtain fractions with specific kinematic viscosities. For example, lubricants with a viscosity Index of 95 and a kinematic viscosity at 100° C. of 4.5 mm 2 per second may be separated in a distillation column into two fractions, a light lubricant and a heavy lubricant. The light lubricants have a boiling range from 343°-427° C. (650-800° F.), while the heavy lubricant have a boiling range from 427-593° C. (800-1100° F.). The light lubricants have a kinematic viscosity at 100° C. of about 3 mm 2 per second and a VI of 95. The heavy lubricants have a kinematic viscosity at 100° C. of about 7 mm$^2$/second.

EXAMPLES

Some illustrative examples are included below that provide details for some of the embodiments described in this document.

Example 1—Distillation of the LFP Liquid Product

Figure 2:
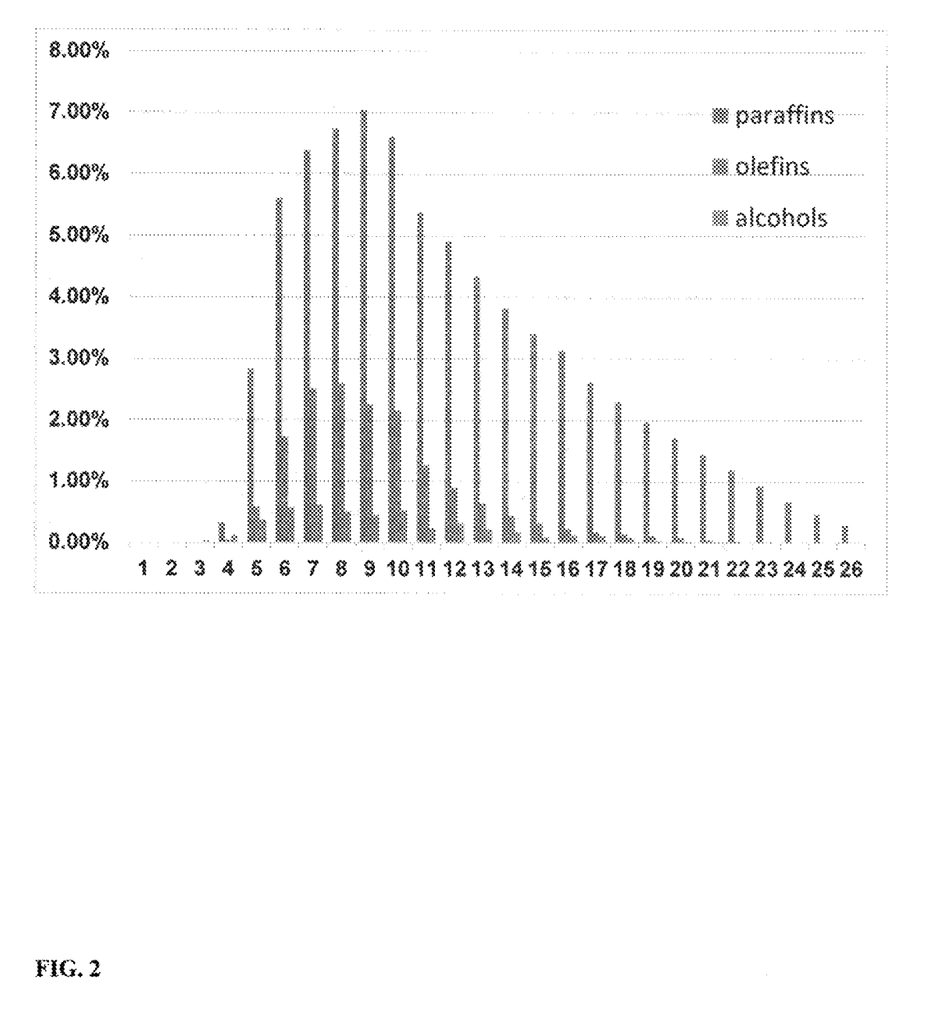
FIG. 2 shows the distribution of normal alkanes (paraffins), normal 1-alkenes, and normal 1-hydroxy alkanes in the LFP liquid product. Paraffins are the highest lines in the groups of three, normal 1-alkenes are the middle-length lines, and 1-hydroxy alkanes are the shortest lines.

About 900 gallons of an LFP liquid product were produced from syngas with an $H_2/CO$ ratio of 1.08 using the following catalyst operating conditions: T: 415° F.; P: 315 psi; SV: 1,750. The normal alkanes, normal 1-alkenes, and normal 1-hydroxy alkanes were separated from the LFP liquid product using a two-step, high efficiency distillation process. The first distillation process employed a 12-inch distillation column packed with 35-feet of vertical stainless-steel packing of Goodloe Style 779 design. This first distillation system was used to generate about 20 sub-fractions from 700 gallons of the LFP liquid product. Each of these fractions was then separated into individual components using a second 35-foot high-efficiency distillation system. The results of this 2-step separation process are summarized in Table 5. The separated normal alkanes, normal 1-alkenes and normal 1-hydroxy-alkanes represent 71.5, 17.4 and 4.8 volume % of the total liquid product. FIG. 2 provides a graphic overview of the products separated from this process.

TABLE 5

The Distribution of Normal Alkanes, Normal 1-Olefins and Normal 1-Hydroxy Alkanes from the Distillation of 700 gallons of the LFP Liquid Product

| Carbon # | Normal Alkanes (gallons) | Normal 1-Olefins (gallons) | Normal 1-Hydroxy Alkanes (gallons) |
| --- | --- | --- | --- |
| C5 | 127.9 | 26.2 | 17.1 |
| C6 | 252.6 | 78.2 | 26.0 |
| C7 | 287.9 | 113.5 | 28.0 |
| C8 | 303.8 | 117.1 | 22.7 |
| C9 | 317.6 | 102.5 | 20.4 |
| C10 | 297.4 | 97.7 | 23.6 |
| C11 | 242.2 | 57.0 | 11.0 |
| C12 | 221.4 | 40.7 | 14.5 |
| C13 | 195.8 | 29.2 | 10.2 |
| C14 | 171.8 | 20.4 | 7.9 |
| C15 | 153.6 | 14.4 | 4.3 |
| C16 | 141.4 | 10.3 | 5.6 |
| C17 | 117.9 | 8.2 | 5.1 |
| C18 | 104.1 | 6.3 | 4.0 |
| C19 | 89.0 | 5.2 | 1.5 |
| C20 | 77.0 | 3.8 | 0.8 |
| C21 | 65.1 | 2.3 | 0.6 |
| C22 | 53.6 | 1.4 | 0.5 |
| C23 | 41.8 | 0.3 | 0.0 |
| Total (gallons) | 511 | 121 | 34 |
| % of total (1) | 71.6 | 17.4 | 4.8 |

Example 2—Composition and Commercial Uses of the Wax Fraction

The synthetic wax product from the LFP conversion process consists of normal aliphatic hydrocarbons that are primarily in the $C_{18}$-$C_{45}$ range (Table 6). This wax doesn't contain any (<1 ppm) cyclic, aromatic and sulfur compounds and the concentration of olefins are very low (<25 ppm).

It has a macro-crystalline structure in which the crystals can be seen without magnification. This wax melts over a 115-145° F. range which is similar to the melting point range of paraffins derived from petroleum (Table 6). However, petroleum derived paraffins are comprised of branched hydrocarbons (iso-alkanes); cyclic and aromatic compounds that typically comprise greater than 25 wt. %. In comparison, this LFP wax contains less than 2 volume % branched (iso) paraffins and no cyclic or aromatic compounds which also improves oxidation stability since iso-alkanes are much easier to oxidize than normal alkanes.

The Sasol and Shell waxes are comprised of $C_{18}$-$C_{100}$ hydrocarbons and the melting point of the un-processed wax is 115-230° F. Therefore, the Sasol and Shells waxes need to be fractionated into light, medium and heavy cuts before they are marketed.

TABLE 6

The Average Properties of Wax produced by the LFP Catalytic Process compared to Other Waxes

| Properties | LFP Process Synthetic Wax | Paraffin (Petroleum) Wax | Sasol & Shell Synthetic Wax |
|---|---|---|---|
| Hydrocarbon Chain Length | $C_{18}$-$C_{45}$ | $C_{18}$-$C_{45}$ | $C_{18}$-$C_{100}$ |
| Density (g/cc) at 68° F. | 0.90 | 0.90 | 0.90 |
| Normal HC's (%) | 95 | <75% | 90 |
| Branched (Iso) HC's (%) | 5 | >15% | 10 |
| Cyclic and Aromatic HC's | <25 ppm | >10% | <25 ppm |
| Crystal Size Classification | Macro | Micro | Micro |
| Melting Temperature (° F.) | 115-145 | 115-150 | 115-230 |
| Sulfur Content | <5 ppm | nd | <5 ppm |
| Alpha-Olefin Content | <25 ppm | nd | <25 ppm |

This LFP Process synthetic wax is expected to be an ideal material:
1. as a rubber additive to prevent cracking
2. for waxing skis and snowboards
3. for protecting and giving a matte finish on painted furniture, cabinets, and walls
4. as a release agent for metal castings
5. for preventing oxidation on steel and iron surfaces
6. for waterproofing leather

U.S. PATENT DOCUMENTS

| | | |
|---|---|---|
| 7,507,326 B1 | March 2009 | Farshid et al |
| 8,394,862 B1 | March 2013 | Schuetzle et al |
| 8,974,660 B1 | March 2015 | Tanaka et al |
| 9,611,145 B1 | April 2017 | Schuetzle et al |
| 9,631,147 B1 | April 2017 | Schuetzle et al |
| 9,896,626 B1 | February 2018 | Schuetzle et al |
| 10,478,806 B1 | November 2019 | Schuetzle et al |

FOREIGN PATENT DOCUMENTS

| | | |
|---|---|---|
| CA 2,936,903 | March 2018 | Schuetzle et al |
| CA 2,904,242 | December 2017 | Schuetzle et al |
| CA 2,948,235 | August 2018 | Schuetzle et al |

OTHER PUBLICATIONS

Ail, S. S., Dasappa, S.: Renewable and Sustainable Energy Reviews 58 267-286 (2016)

De Klerk, A.: Fischer-Tropsch Refining, University of Pretoria, South Africa (2008)

Fedou at al: Conversion of syngas to diesel, Axens, www.axens.net (2020)

Gruber, H. et al: Fischer-Tropsch products from biomass-derived syngas and renewable hydrogen, Biomass Conversion and Biorefinery (2019)

Li, W., Wang, H., Jiang, X., Zhu, J., Liu, Z., Guo, X., Song, C.: A short review of recent advances in $CO_2$ hydrogenation to hydrocarbons over heterogeneous catalysts, RSC Adv., 8, 7651 (2018)

Schuetzle, D., Tamblyn, G., Caldwell, M., Schuetzle, R.: Solar reforming of carbon dioxide to produce diesel fuel. DOE report #DE-FE0002558 (2010)

Zhu, Q.: Developments on $CO_2$ Utilization technologies, Clean Energy, 3, 85-100 (2019)

The invention claimed is:

1. A process for production of chemicals, wherein the process comprises the following: feeding a feedstock comprising hydrogen and carbon monoxide to a liquid fuel production reactor, wherein the liquid fuel production reactor comprises a catalyst, thereby producing a product, wherein the product comprises a liquid phase and a solid phase, and wherein the liquid phase comprises C5-C23 hydrocarbons and oxygenated hydrocarbons, and wherein the solid-phase comprises C24-C45 aliphatic hydrocarbons, and wherein the liquid phase is between 51 percent by volume and 99 percent by volume of the product, wherein the liquid phase comprises olefins, and wherein the olefins are fed to an oligomerization reactor comprising an oligomerization catalyst to produce the chemicals, and wherein the oligomerization catalyst comprises chromium impregnated on a silica substrate.

2. The process of claim 1, wherein the liquid fuel production reactor is operated at 375-450° F., 150-450 psi and 750-10,000 space velocity.

3. The process of claim 1, wherein the volume/volume ration of hydrogen to carbon monoxide fed into the liquid fuel production reactor ranges from 0.5 to 2.5.

4. The process of claim 1, wherein the liquid phase comprises between 95 and 99 volume percent of the product, and wherein the solid phase comprises between 5 percent and 1 percent of the product, and wherein the liquid fuel production reactor is operated at 400-420° F., 300-350 psi and 1,500-3,000 space velocity.

5. The process of claim 1, wherein the liquid phase contains between 45 volume percent and 85 volume percent of C5-C23 aliphatic hydrocarbons.

6. The process of claim 1, wherein the liquid phase contains between 2 volume percent and 40 volume percent of C5-C16 normal 1-alkenes.

7. The process of claim 1, wherein the liquid phase comprises between 1 volume percent and 8 volume percent of C3-C16 normal 1-hydroxy alkanes.

8. The process of claim 1, wherein the solid phase comprises between 95 volume percent and 99 volume percent of normal alkenes.

9. The process of claim 1, wherein the concentration of C5-C16 normal 1-alkenes in the liquid phase is dependent on the ratio of hydrogen to carbon monoxide that is fed into the liquid fuel production reactor, and wherein when the ratio is reduced the amount of C5-C16 normal 1-alkenes is increased.

10. The process of claim 1, wherein the concentration of C24-C45 normal aliphatic hydrocarbons in the solid phase is dependent on the ratio of hydrogen to carbon monoxide that is fed into the liquid fuel production reactor, and wherein when the ratio is reduced the amount of C24-C45 normal aliphatic hydrocarbons is increased.

11. The process of claim 1, wherein the liquid product is distilled into three fractions, wherein the three fractions are a naphtha fraction comprising C5-C9 hydrocarbons and oxygenated hydrocarbons, a diesel fuel fraction comprising C9-C23 hydrocarbons and oxygenated hydrocarbons and a solid phase fraction comprising C24-C25 hydrocarbons.

12. The process of claim 5, wherein the C5-C23 aliphatic hydrocarbons are separated into fractions using either distillation or adsorbents.

13. The process of claim 6, wherein the C5-C16 normal 1-alkenes are separated into fractions using either distillation or adsorbents.

14. The process of claim 7, wherein the C3-C16 normal 1-hydroxy alkanes are separated into fraction using either distillation or adsorbents.

15. The process of claim 11, wherein the napththa fraction, the diesel fuel fraction and the solid phase fraction each have a purity between 95% and 99%.

16. The process of claim 12, wherein the fractions each have a purity between 95% and 99%.

17. The process of claim 13, wherein the fractions each have a purity between 95% and 99%.

18. The process of claim 14, wherein the fractions each have a purity between 95% and 99%.

19. The process of claim 5, wherein C5-C16 normal alkenes in the liquid phase are converted to normal 1-hydroxy alkanes by catalytic hydration.

20. The process of claim 6, wherein normal 1-hydroxy alkanes in the liquid phase are converted to normal 1-alkenes by catalytic dehydration.

21. The process of claim 19, wherein the 1-hydroxy alkanes are separated from unconverted liquid phase.

22. The process of claim 20, wherein the normal 1-alkenes are separated from unconverted liquid phase.

23. The process of claim 3, wherein the hydrogen fed into the liquid fuel production reactor is produced from electrolyzing water using renewable power.

24. The process of claim 3, wherein the hydrogen and carbon monoxide fed into the liquid fuel production reactor is produced from the catalytic conversion of hydrogen and carbon dioxide, and wherein the hydrogen is produced from electrolyzing water using renewable power.

* * * * *